(12) United States Patent
Davenport et al.

(10) Patent No.: US 9,289,312 B2
(45) Date of Patent: Mar. 22, 2016

(54) SPINAL IMPLANTS WITH STEM CELLS

(75) Inventors: Alan Davenport, Flowery Branch, GA (US); Tracy Scott Anderson, Atlanta, GA (US); Jeffrey Scott Radcliffe, Marietta, GA (US)

(73) Assignee: Vivex Biomedical, Inc., Marietta, GA (US)

( * ) Notice: Subject to any disclaimer, the term of this patent is extended or adjusted under 35 U.S.C. 154(b) by 457 days.

(21) Appl. No.: 13/546,430

(22) Filed: Jul. 11, 2012

(65) Prior Publication Data

US 2013/0018471 A1 Jan. 17, 2013

Related U.S. Application Data

(60) Provisional application No. 61/507,310, filed on Jul. 13, 2011.

(51) Int. Cl.
*A61F 2/44* (2006.01)
*A61L 27/04* (2006.01)
(Continued)

(52) U.S. Cl.
CPC ............... *A61F 2/447* (2013.01); *A61F 2/4455* (2013.01); *A61L 27/042* (2013.01); *A61L 27/06* (2013.01); *A61L 27/18* (2013.01); *A61L 27/3834* (2013.01); *A61F 2/4684* (2013.01); *A61F 2002/2817* (2013.01); *A61F 2002/2835* (2013.01); *A61F 2002/30477* (2013.01); *A61F 2002/30604* (2013.01); *A61F 2002/30607* (2013.01); *A61F 2002/30609* (2013.01); *A61F 2002/30611* (2013.01); *A61F 2002/30612* (2013.01); *A61F 2002/30616* (2013.01); *A61F 2002/30774* (2013.01); *A61F 2002/30784* (2013.01); *A61F 2002/30836* (2013.01);

(Continued)

(58) Field of Classification Search
CPC ............ A61F 2/447; A61F 2002/4475; A61L 27/3834
USPC ................................ 623/17.11–17.16; 606/70
See application file for complete search history.

(56) References Cited

U.S. PATENT DOCUMENTS 6,174,333 B1 1/2001 Kadiyala
6,254,637 B1 7/2001 Lee
(Continued)

FOREIGN PATENT DOCUMENTS

CN 101579537 11/2009
WO 03083088 10/2003
(Continued)

OTHER PUBLICATIONS

Bearingworks.com; PEEK Data Sheet; available as of Sep. 2010; accessed Sep. 15, 2015. http://www.bearingworks.com/content_files/pdf/retainers/PEEK%20datasheet.pdf. Relevant data at pp. 1 of 3.*

*Primary Examiner* — David Bates
(74) *Attorney, Agent, or Firm* — David L. King

(57) ABSTRACT

A spinal implant device has a synthetic or metallic or a combination thereof of these materials in an implant body structure and stem cells in a coating, or a sheet, wrap or a membrane wrap applied to surfaces on the implant body structure or alternatively filled with a plug of stem cell laden material. The implant body structure preferably has an aperture or channel. The spinal implant device may include anchoring holes to secure the device to the spinal skeletal structure with fasteners or alternatively can simply be held in place by and between adjacent vertebrae.

20 Claims, 10 Drawing Sheets

(51) Int. Cl.
*A61L 27/06* (2006.01)
*A61L 27/18* (2006.01)
*A61L 27/38* (2006.01)
*A61F 2/30* (2006.01)
*A61F 2/46* (2006.01)
*A61F 2/28* (2006.01)

(52) U.S. Cl.
CPC ............ *A61F 2002/30841* (2013.01); *A61F 2002/30843* (2013.01); *A61F 2002/30904* (2013.01); *A61F 2002/30912* (2013.01); *A61F 2002/30914* (2013.01); *A61F 2002/30915* (2013.01); *A61F 2002/30971* (2013.01); *A61F 2002/30973* (2013.01); *A61F 2002/4475* (2013.01); *A61F 2002/4495* (2013.01); *A61F 2310/00017* (2013.01); *A61F 2310/00023* (2013.01); *A61F 2310/00389* (2013.01); *A61F 2310/00976* (2013.01); *A61L 2430/38* (2013.01)

(56) References Cited

U.S. PATENT DOCUMENTS

| | | | | |
|---|---|---|---|---|
| 6,261,586 | B1* | 7/2001 | McKay | 424/423 |
| 6,371,988 | B1* | 4/2002 | Pafford et al. | 623/17.11 |
| 6,541,024 | B1* | 4/2003 | Kadiyala | C12N 5/0663 424/426 |
| 6,863,900 | B2 | 3/2005 | Kadiyala | |
| 7,923,246 | B2 | 4/2011 | Sasai | |
| 8,414,654 | B1* | 4/2013 | Ganey | A61F 2/28 623/16.11 |
| 8,758,448 | B2* | 6/2014 | Matheny | A61K 35/12 424/443 |
| 9,011,537 | B2* | 4/2015 | Wei | A61F 2/4603 623/16.11 |
| 9,066,993 | B2* | 6/2015 | Matheny | A61L 31/005 |
| 2002/0143400 | A1 | 10/2002 | Biscup | |
| 2003/0180263 | A1* | 9/2003 | Geistlich | A61L 27/24 424/93.7 |
| 2004/0193270 | A1* | 9/2004 | DiMauro et al. | 623/17.11 |
| 2004/0193274 | A1* | 9/2004 | Trieu | A61F 2/442 623/17.16 |
| 2004/0259972 | A1* | 12/2004 | Ringeisen et al. | 523/113 |
| 2005/0070900 | A1* | 3/2005 | Serhan et al. | 606/61 |
| 2005/0154463 | A1* | 7/2005 | Trieu | A61F 2/441 623/17.16 |
| 2006/0159668 | A1* | 7/2006 | Geistlich | A61L 27/20 424/93.7 |
| 2006/0276788 | A1 | 12/2006 | Berry | |
| 2006/0276793 | A1* | 12/2006 | Berry | 606/69 |
| 2006/0293749 | A1 | 12/2006 | Hudgins | |
| 2007/0100455 | A1 | 5/2007 | Parsons | |
| 2007/0141036 | A1 | 6/2007 | Gorrochategui | |
| 2008/0097618 | A1 | 4/2008 | Baker | |
| 2008/0119853 | A1 | 5/2008 | Felt | |
| 2009/0105825 | A1* | 4/2009 | Foreman | A61F 2/4465 623/17.16 |
| 2009/0175954 | A1 | 7/2009 | Kinoshita | |
| 2009/0198339 | A1 | 8/2009 | Kleiner | |
| 2009/0209031 | A1 | 8/2009 | Stopek | |
| 2009/0238855 | A1 | 9/2009 | Matheny | |
| 2009/0254182 | A1* | 10/2009 | Kovarik | A61F 2/4611 623/17.11 |
| 2009/0318962 | A1 | 12/2009 | Spedden | |
| 2010/0023129 | A1 | 1/2010 | Xu | |
| 2010/0034864 | A1 | 2/2010 | Spedden | |
| 2010/0196437 | A1 | 8/2010 | Dinh | |
| 2010/0203101 | A1 | 8/2010 | Cancedda | |
| 2012/0010715 | A1* | 1/2012 | Spann | A61B 17/02 623/17.16 |
| 2012/0226319 | A1* | 9/2012 | Armstrong et al. | 606/279 |
| 2012/0271361 | A1* | 10/2012 | Zhou et al. | 606/304 |
| 2012/0277866 | A1* | 11/2012 | Kalluri et al. | 623/17.16 |
| 2013/0268075 | A1* | 10/2013 | Mckay | A61F 2/447 623/17.16 |

FOREIGN PATENT DOCUMENTS

| | | |
|---|---|---|
| WO | 2005040361 | 5/2005 |
| WO | 2010054527 | 5/2010 |

* cited by examiner

SPINAL IMPLANTS WITH STEM CELLS

RELATED APPLICATIONS

The present invention claims benefit of priority to U.S. provisional application No. 61/507,310 filed on Jul. 13, 2011 entitled "Spinal Implants With Stem Cells.

TECHNICAL FIELD

The present invention relates to spinal implant devices generally. More specifically to synthetic or metal implants wrapped or coated with stem cells.

BACKGROUND OF THE INVENTION

It is recognized that stem cell therapies have had beneficial healing effects in relation to wound healing. The wound, whether caused by trauma or as part of a surgical procedure, appears and has been proven to heal more rapidly with the beneficial use of sutures laden with stem cells. As early as Jan. 16, 2001 a patent was granted and publicly released called Biomatrix for soft tissue regeneration using mesenchymal stem cells which was U.S. Pat. No. 6,174,333 B1. This work was in conjunction with Case Western University and Osiris Therapeutics Inc. and disclosed the manufacture of a mat sheet that was formed into a spiral roll with sutures extending from opposite roll ends to form an implant laden with stem cells.

The implant for repair of a tissue defect used a plurality of physiologically compatible load-bearing sutures for securing under tension tissue adjacent to the defect to be repaired, the sutures for supporting a tissue reparative cell mass in the defect and a tissue reparative cell mass supported thereby. The sutures had a central portion encapsulated in a cell containing matrix which is contracted under a tensile load by the cells thereof and formed into a mat sheet during the contraction. Spring metal wires hold the sutures in tension during the contraction. The matrix was a collagen gel or other material which the cells contract, the cells comprising human mesenchymal stem cells.

Latter inventors working for Bioactive Surgical, Inc. disclosed in US 2009/0318962 surgical sutures incorporated with cells or other bioactive materials. The stem cell laden sutures allowed medical personnel to reintroduce bioactive material extracted from a patient or the allogenic equivalents to a wound or surgical site.

All of this work involved using stem cell laden sutures to accelerate wound healing typically and were directed to soft tissue.

In WO 2010054527 the use of stem cells was taught to be beneficial in jaw bone prosthesis. These prostheses. These prostheses were implants made of human tissue taken from cadavers.

In U.S. Pat. No. 6,254,637 taught that a very thin artificial cornea was implanted on the surface of an eye and covered by an amnion sheet in an attempt to promote a stable graft.

As the science of stem cell production and manufacture has been evolving, the technology has developed techniques to provide methods for culturing stem cells with the use of amnion membranes as in U.S. Pat. No. 7,923,246 or as taught in US 2009/0175954A and US 2009/0238855 the manufacture of stem cell laden sheets have been successfully produced.

This ability to provide sheets or even coatings of stem cell laden material has given the surgeon a new tool to use in combination with soft tissue or organ implants to reduce rejection and accelerate healing. Collagen laden stem cell sutures are available for artery or vein repair and the wraps have been proposed to accelerate bone fracture healing. In all of these uses it has been proposed that stem cells could help in tissue to cellular tissue regeneration and healing.

The present invention proposes a new and beneficial use of stem cell coatings or preferably stem cell wraps in pliable sheet form as disclosed and described below.

SUMMARY OF THE INVENTION

A spinal implant device has a synthetic or metallic or a combination thereof of these materials in an implant body structure and stem cells in a coating, or a sheet, wrap or a membrane wrap applied to surfaces on the synthetic or metallic or both implant body structure or alternatively filled with a plug of stem cell laden material. The implant body structure preferably has an aperture or channel.

The body structure can be made of an implantable grade synthetic plastic, which is a thermoplastic or thermoset material. The plastic material can be any implantable grade material such as PEEK (polyether ether ketone), polyethylene, ultra high molecular weight polyethylene, polyphenylsulfone, polysulfone, polythermide, acetal copolymer, polyester woven or solid or implantable grade lennite UHME-PE. Alternatively, the implant body structure can be made of stainless steel or titanium or any other acceptable implantable metallic material. The spinal implant device may include anchoring holes to secure the device to the spinal skeletal structure with fasteners or alternatively can simply be held in place by and between adjacent vertebrae.

The spinal implant device may be pre-packaged as a kit with the body structure and the coating, sheet or membrane wrap laden with stem cells in a separate container to be applied to the body structure during the surgical procedure. Alternatively, the surgical implant device may be sterilized and then coated or wrapped or filled with a plug molded in the channel of the implant device with the stem cell laden material and packaged together in a sterile package or container. The package or container may be sterile dry filled which may require re-hydrating the coated or wrapped implant or alternatively the spinal implant with a stem cell laden coating or wrap could be sterile liquid filled in which case the implant device can be directly implanted.

The device permits several methods for treating a patient in need of a spinal implant. One method has the steps of preparing the patient to receive a spinal implant by surgically exposing the area to receive the spinal implant, the spinal implant having a synthetic or metallic or both body structure, coating or wrapping the body structure of the spinal implant, the coating or wrapping being a material laden with stem cells, implanting the coated or wrapped spinal implant and may also include hydrating the stem cell laden coating or wrap before wrapping the implant.

Alternatively, the pre-applied stem cell laden spinal implant device simplifies the method by simply preparing the patient and implanting the spinal implant device pre-coated or wrapped with a stem cell laden material. This simplified procedure can require hydrating the implant if packaged dry or may not even require that additional step.

BRIEF DESCRIPTION OF THE DRAWINGS

The invention will be described by way of example and with reference to the accompanying drawings in which.

DETAILED DESCRIPTION OF THE INVENTION

Figure 1:
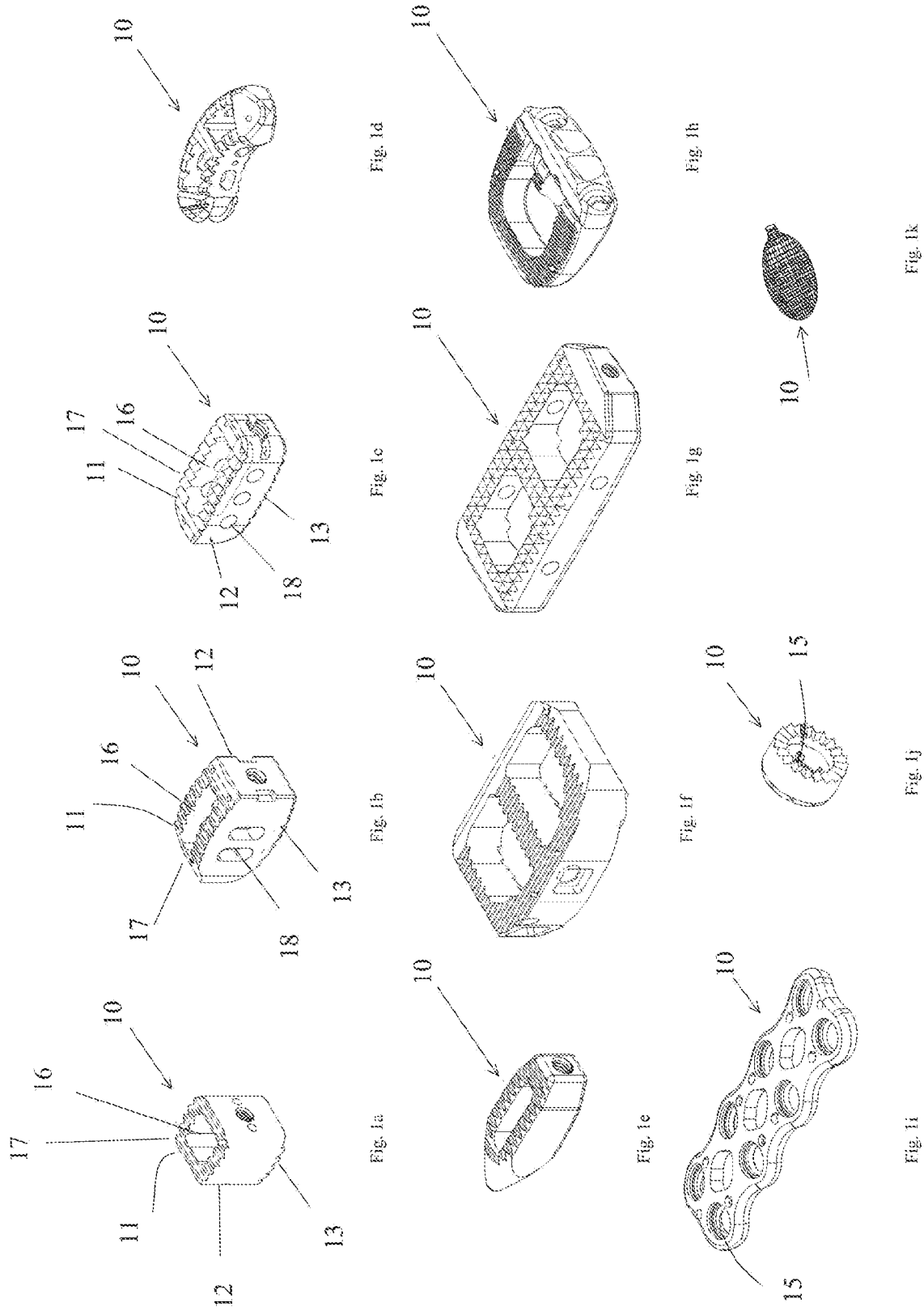
FIGS. 1a-1k are a number of perspective views of exemplary synthetic, metallic or a combination thereof spinal implants that can be made according to the present invention.

With reference to FIGS. 1a-1k, a number of perspective views of exemplary synthetic metallic or combinations thereof of spinal implants that are made according to the present invention are illustrated. Each of the implants 10 as shown has a metallic, synthetic or combination of metallic and synthetic implant body structures 12. The implant body structures 12 as shown are designed for insertion on or into a skeletal spinal structure of a patient. FIG. 1a is the Phenix CID, FIG. 1b is the Talos-P PLIF, FIG. 1c is the TLIF, FIG. 1d is Talos-T TLIF, FIG. 1e is entitled OLIF, FIG. 1f is Talos-A ALIF, FIG. 1g is LLIF, FIG. 1h is Thor Standalone ALIF, FIG. 1i is the Diamond Cervical Plate, FIG. 1j is the Facet Screw Skirt and FIG. 1k is a synthetic woven pouch used in bone grafting and repair.

Each of these exemplary spinal implant device examples are manufactured and sold by Amendia or are competitor's alternatives that are also available for this purpose. For the purposes of simplification, each of these devices are commonly referred to by reference numeral 10 for the device and 12 for its body structure even though they are structurally not the same in appearance each device 10 shown in FIGS. 1a-1k is designed to function as a spinal implant device made in accordance to the present invention.

With reference to FIG. 1a, the Phenix CID, Phenix™—Cervical Interbody Device: Is a rectangular implant comprised of PEEK-OPTIMA® polymer from Invibio Biomaterial Solutions, a radiolucent material with properties that match the modulus of elasticity of cortical bone. The Phenix™ is intended for use with supplemental spinal fixation systems that have been labeled for use in the cervical spine. The Phenix "PEEK-OPTIMA® polymer from Invibio Biomaterial Solutions Cervical Interbody Device is available in a range of sizes and heights to fit any anatomy and includes heights up to 12 mm. Available sizes range from a traditional 12 mm×12 mm implant for small vertebral bodies to a 17 mm wide×14 mm A/P implant that sits at the load bearing perimeter of the vertebral body and contains a large graft window.

With reference to FIG. 1b, the Talos-P PLIF, the Talost-P is a PEEK-OPTIMA lumbar interbody device for PLIF approach. This cage is available in 3 lengths, 2 widths and a complete range of heights with instrumentation that combines with the Talos®-T in one set to provide a complete Posterior and Transforaminal solution.

With reference to FIG. 1d, the Talos-T TLIF, The Talos®-T is a PEEK-OPTIMA lumbar interbody device for TLIF approach. The Talos-T is a curved cage with a functional system for guiding the implant to a proper position. The instrumentation of the Talos®-T is combined with the Talos®-P instrument set to provide a flexible solution for Posterior and Transforaminal approaches. It includes angled teeth prevent implant migration, tapered nose aids in insertion and distraction, angled shape improves fit between vertebral bodies, functional tamps guide implant to proper position and tantalum markers.

With reference to FIG. 1e, the Talos-O OLIF, the Talos®-O is a truly unique percutaneous PEEK-OPTIMA lumbar interbody device that is delivered through an oblique approach. This interbody is delivered through an annular incision that is anterior to the transverse process, and is totally percutaneous. The PEEK-OPTIMA implant distracts and provides unquestioned rigid anterior support for the vertebral body. This oblique approach is achieved for all lumbar segments, including the L5-S1 disc space. Our discectomy instruments work through the small access portal to provide a complete percutaneous discectomy. Implants are available in lengths and heights to accommodate all varieties of lumbar interbody spaces. It includes percutaneous delivery, distracts Intervertebral space, anatomically designed for implantation, Instrumentation for percutaneous discectomy, tapered shape glides past the nerve root, cannulated delivery preserves safe pathway to the disc space, angled teeth prevent implant migration and tantalum markers.

With reference to FIG. 1f, the Talos-A ALIF, the Talos®-A is a traditional ALIF interbody device that is available in a range of sizes to accommodate every anatomic requirement. Instrumentation is provided for delivery from an Anterior or Anterolateral approach. A variety of lordotic angles and sizes are available. It includes chamfered corners provide anatomical fit, angled teeth prevent implant migration, two insertion options for anterior or santerolateral approaches, lordotic angles to match spinal anatomy, implant trials and rasps for preparing disc space and tantalum markers.

With reference to FIG. 1i, the Diamond Cervical Plate, the Diamond Anterior Cervical Plate is a world class cervical plating system utilizing a unique self-locking mechanism that is effortless to engage and offers superior screw retention while providing a simple revision technique. The Diamond Cervical Plate is offered in single through four level varieties and has the option of fixed or variable screws, and self-tapping or self-drilling. Rescue screws are also provided. Benefits include; superior back-out resistance, fixed and variable screws for rigid, dynamic, or hybrid stabilization, variable screws allow 30 degrees of freedom, low profile, easy to revise, color-coding of screws for length and fixed/variable head identification, instrumentation designed to reduce surgical steps, diamond window allows for greater graft visualization and self-drilling tip or conservative self-tapping tip.

FIG. 1k shows a surgical mesh made of a Polyethylene Terephthalate (PET) mesh pouch designed to contain impacted granular bone graft and enable its incorporation. The mesh is used most commonly for traumatic fracture repair and interbody fusion.

As shown in FIGS. 1a through 1h, each of the body structures 12 is provided with at least one vertically oriented channel 16 or aperture which extends through the implant device 10. These channels 16 are provided to enable bone tissue or bone graft material to be inserted into the device during a surgical procedure. Some of the exemplary embodiments have a lateral or side opening or channel 18. The side openings or channels 18 are provided to enable an x-ray to pass through the implant device in order to establish bone formation in the patient after surgery has been completed and the implant has been inserted for a period of time. Additionally, some implants 10 may have holes 15 such as in the diamond cervical plate 10 of FIG. 1*i* threaded or otherwise to allow the device 10 to be secured or anchored to the spinal skeleton structure between adjacent vertebrae if so desired. Several of the devices are shown with jagged or toothed outer surface 17 on the upper surface 11 and lower surface 13, these features help the device 10 to engage the vertebrae when implanted and help hold the device 10 into position between adjacent vertebrae during the surgical procedure. The exterior surface of the body structures 12 of each of these devices can be coated with a coating 22 gel or spray of a biological substance or material containing stem cells 21 when made according to the present invention.

Figure 2:
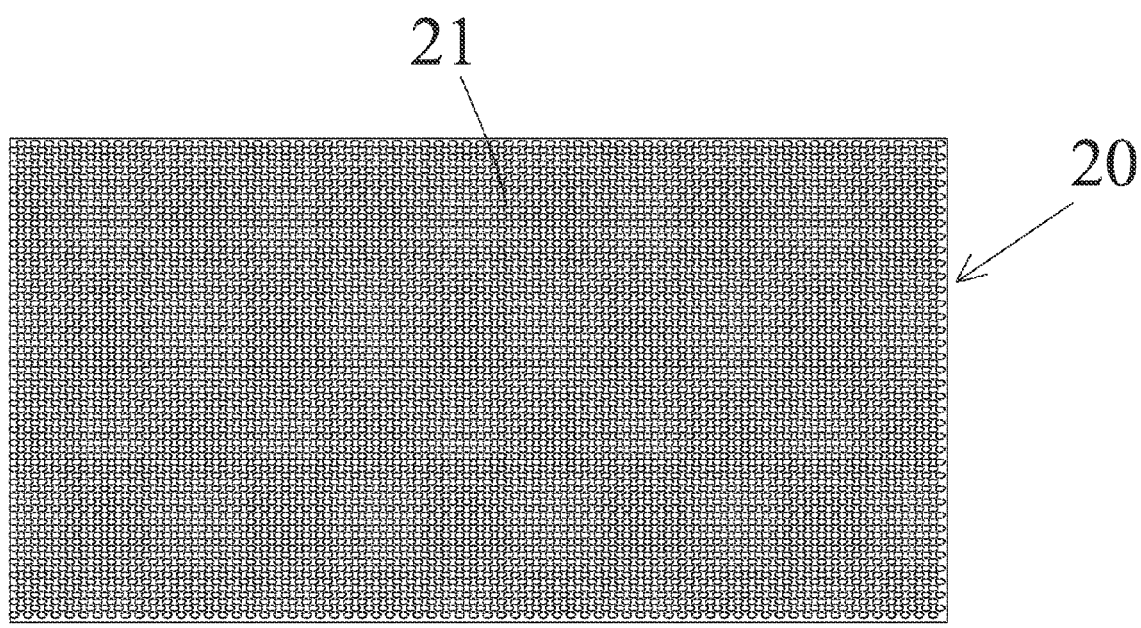
FIG. 2 is a depiction of a stem cell laden sheet or membrane material that can be used in the spinal implant made according to the present invention.

Alternatively, as illustrated in FIG. 2, a sheet or membrane 20 of material can be provided that is laden with stem cells 21. This sheet or membrane 20 can be wrapped around each of the exemplary implant devices 10 at the time of surgery if so desired. Alternatively, as will be discussed later the sheet or membrane 20 can form a wrap around the implant device 10 which can be pre-assembled at a manufacturing facility in a sterile environment, packaged and shipped to the medical facility for direct use as a surgical implant with a stem cell laden sheet or wrap membrane 20 material wrapped about the outer surface of the implant device 10. It is this combination of the implant device 10 with a coating of stem cells 21 or a wrap 20 of stem cell material that provides an enhanced ability of the implant to be accepted by the patient in order for the implant to be fused by bone growth between vertebrae if so desired.

Typically the channels of the implant devices 10 are filled with bone graft material either in a paste form or in solid bone material. This material during the patient's healing is expected to fuse with the adjacent vertebrae and by providing an envelope or covering of stem cells on the implant it is believed that the implant device 10 will be more quickly fused to the spinal skeletal structure in a faster more rapid fashion due to the ability of the stem cells to trigger the regenerative process and to allow the adjacent bone structure to grow around the implant device more quickly than would occur otherwise in the absence of the stem cell wrap 20 or coating 22.

Figure 3:
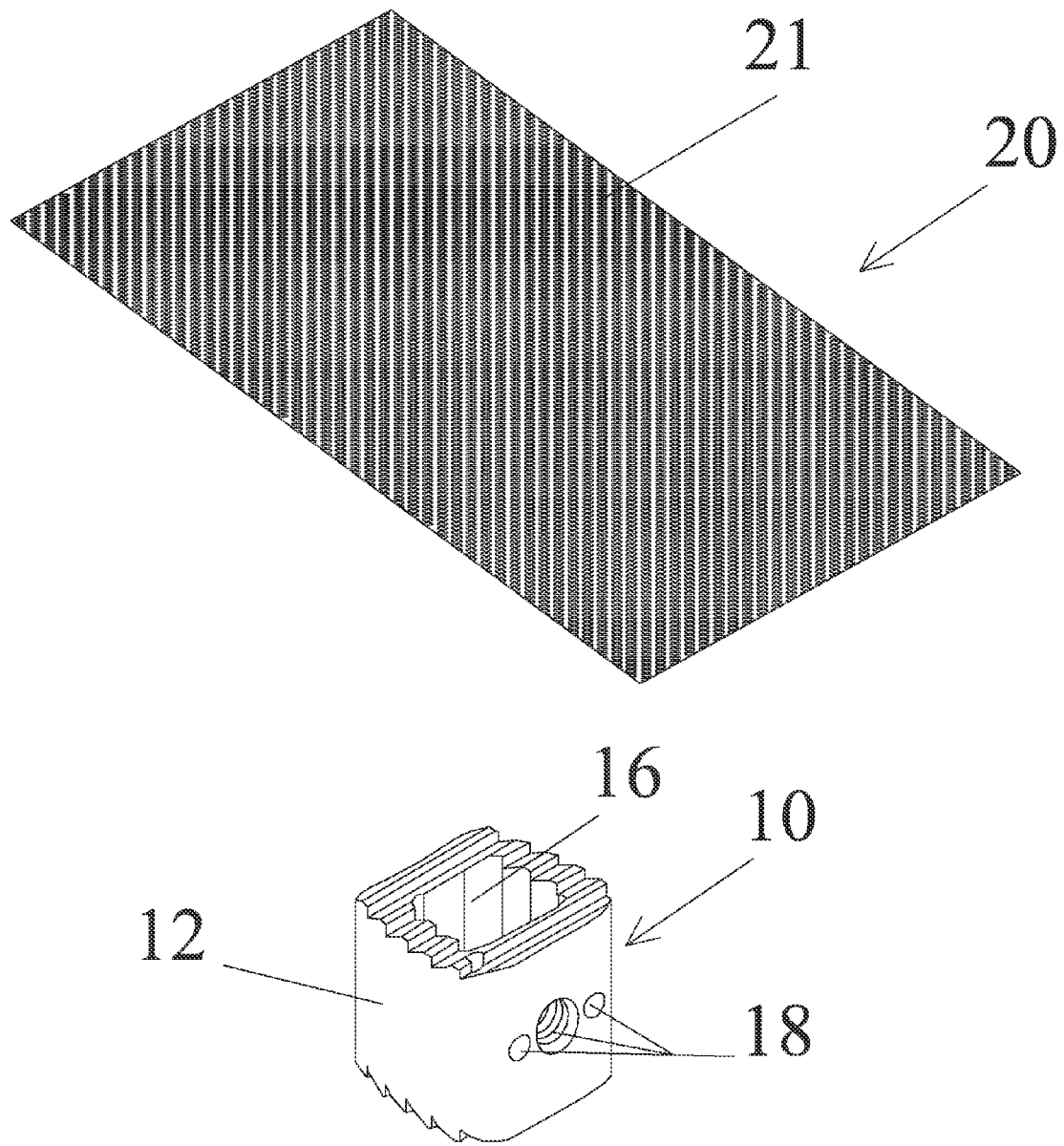
FIG. 3 is an exploded view of an exemplary pre-packaged kit with the spinal implant wrapped with a stem cell sheet or membrane according to the present invention.

With reference to FIGS. 3-7, a variety of ways are proposed which facilitate shipping the spinal implant device 10 made according to the present invention as a prepackaged kit for use in the surgical operating room. As shown in FIG. 3, the kit can include the spinal implant device 10 with a separate stem cell laden wrap 20 included. These devices 10 and 20 when assembled as a kit can then be taken to an operating room and opened in an aseptic technique. The implant device 10 preferably is prepackaged in a separate package as well as the stem cell laden wrap 20 being separately packaged in a package.

Figure 4:
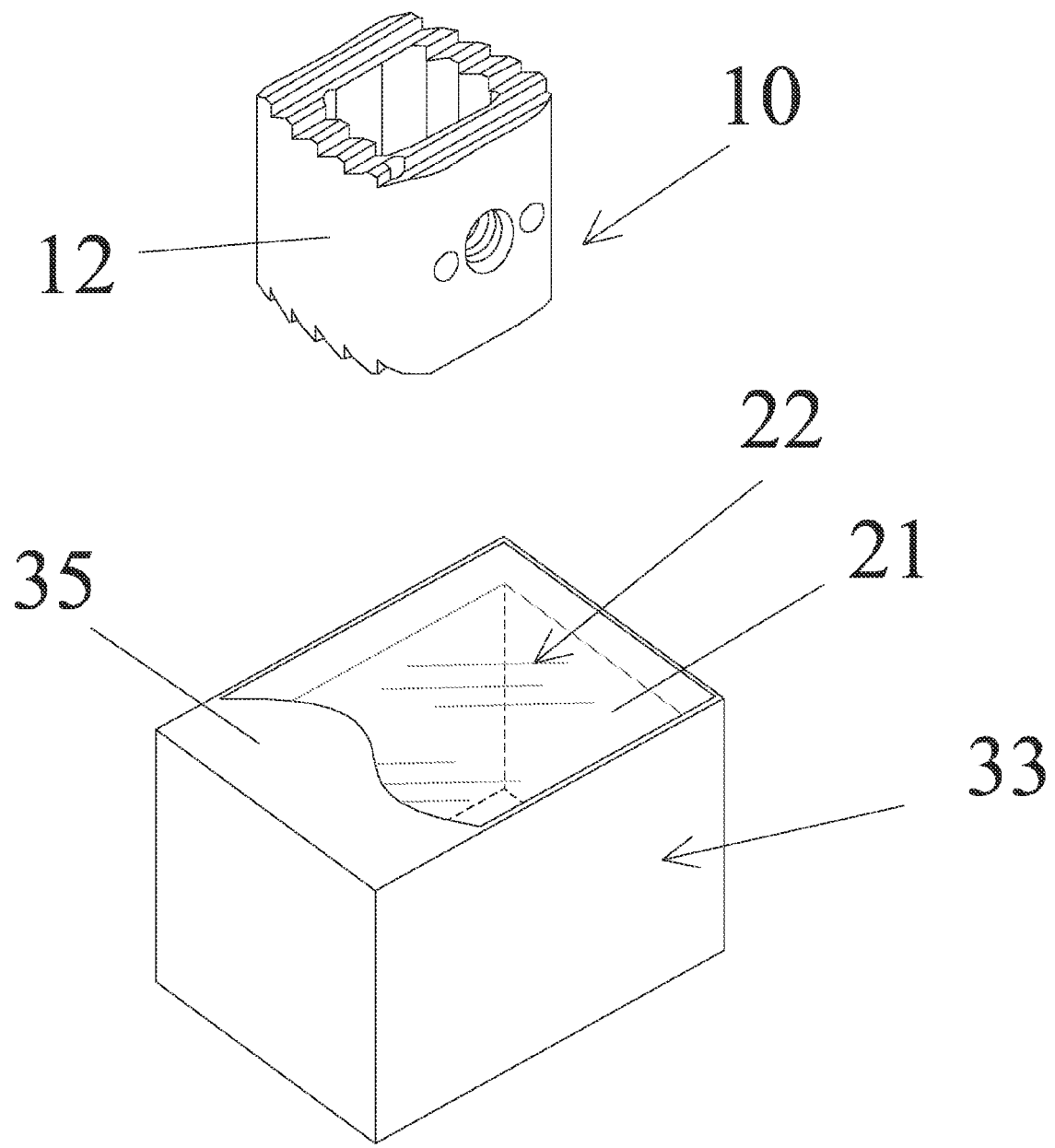
FIG. 4 is an exploded view of an alternative embodiment pre-packaged kit with the spinal implant and a separate container with a stem cell laden coating in liquid or gel form.
Figure 5:
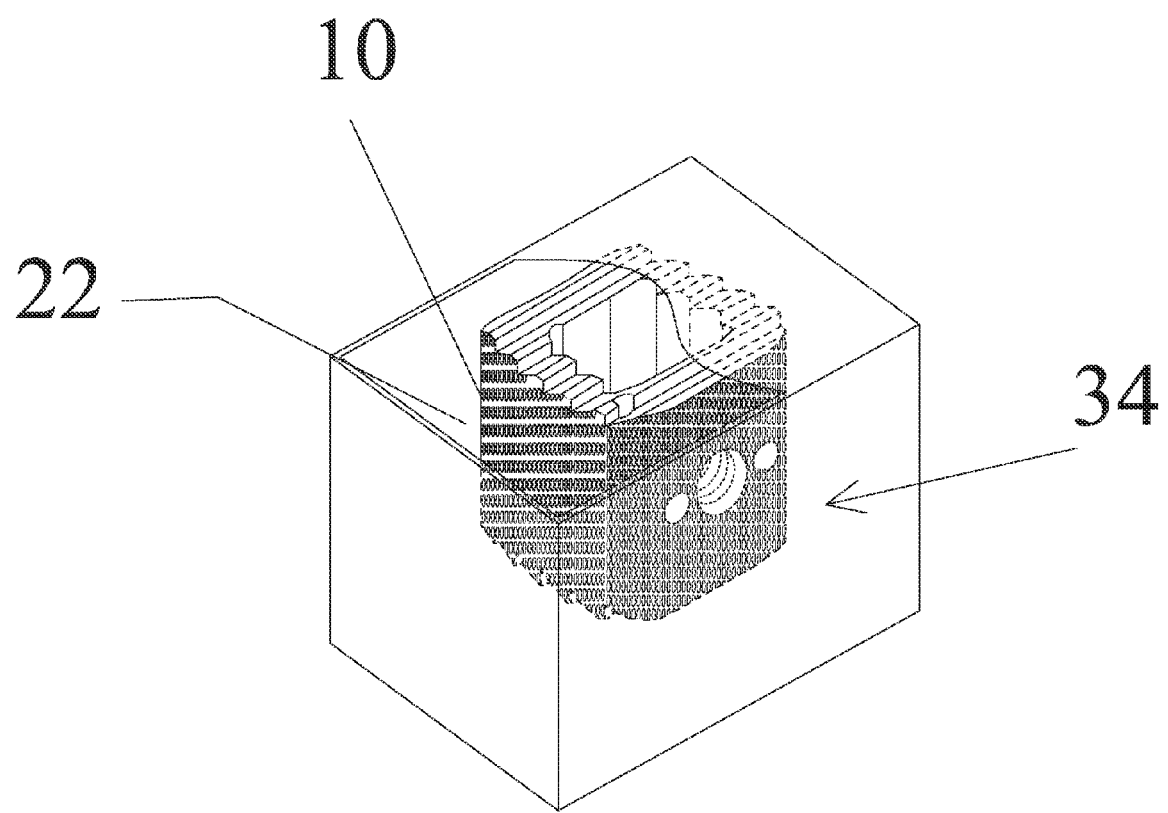
FIG. 5 is an exploded view of a sterile pre-packaged spinal implant with a coating applied.
Figure 6:
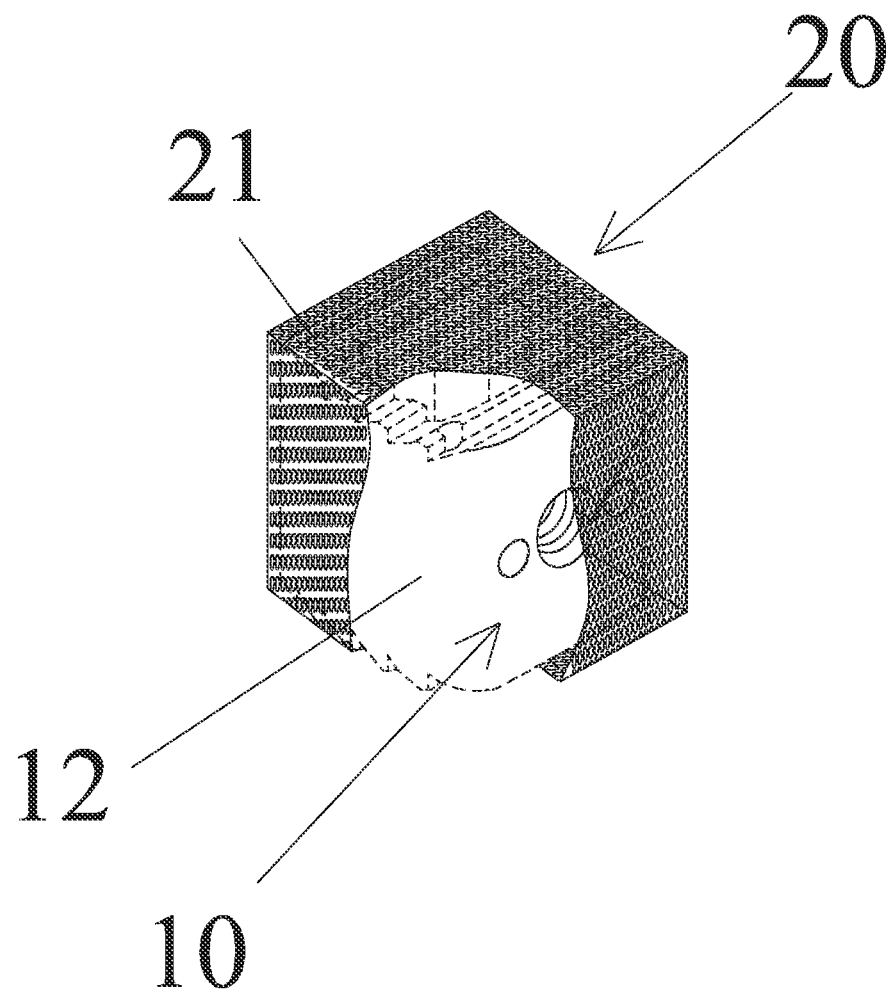
FIG. 6 is an exploded view of a sterile spinal implant covered with a stem cell laden wrap.
Figure 8:
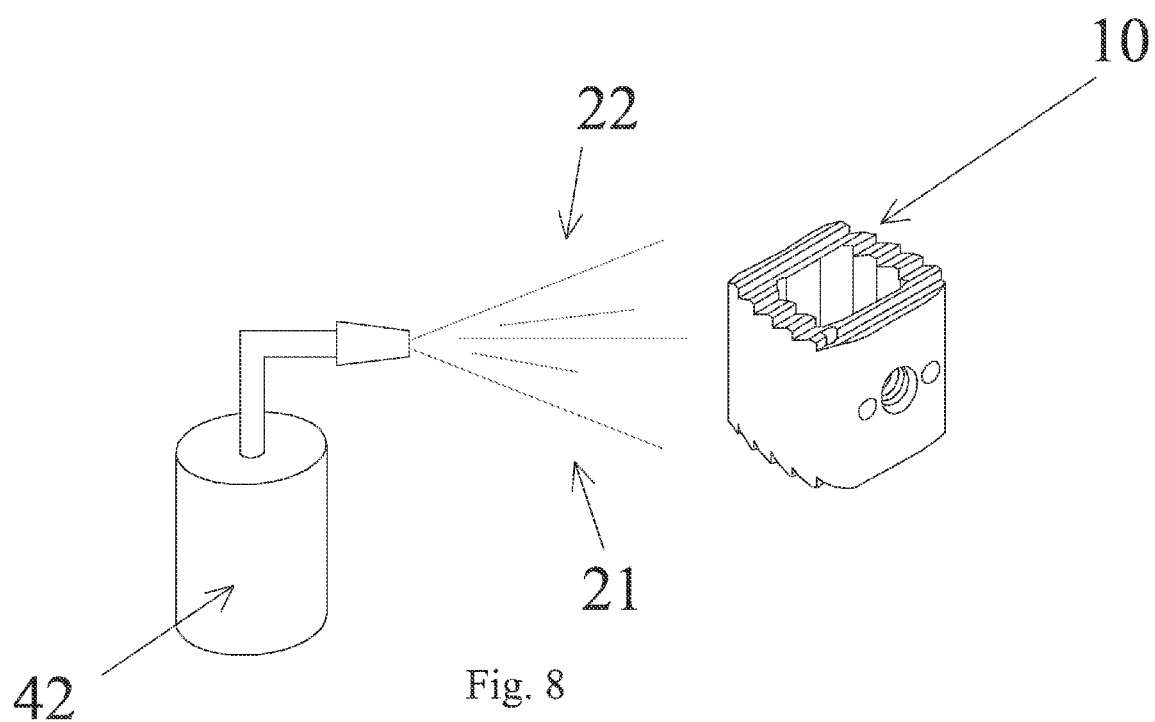
FIG. 8 is a perspective view of the spinal implant shown being spray coated with a mist laden with stem cells.

In FIG. 4, an alternative embodiment is shown with a prepackaged kit wherein the spinal implant 10 can be separately packaged and a separate container 33 is provided filled with a stem cell laden coating 22 either in a liquid or gel form. As shown this container 33 can be provided with a sealed lid 35 in such a fashion that the implant device 10 can be dipped into the stem cell 21 laden coating material 22 or alternatively as shown in FIG. 8 can be provided in a spray device wherein the stem cells 21 can be sprayed directly onto the implant device 10 in a sterile and aseptic technique used in the operating room. Alternatively, as shown in FIG. 5, a prepackaged kit can be made where the spinal implant 10 is placed in a prepackaged container 34 with the coating 22 already applied. Alternatively, as shown in FIG. 6, the spinal implant device 10 can also be prepackaged and covered with the stem cell laden 20 wrap if so desired. In both FIGS. 5 and 6, this prepackaging of the stem cells 21 requires that the spinal implant 10 be made in an aseptic or clean room environment in the absence of any secondary sterilization that might impede or kill the stem cells coated or otherwise wrapped onto the device.

Figure 7:
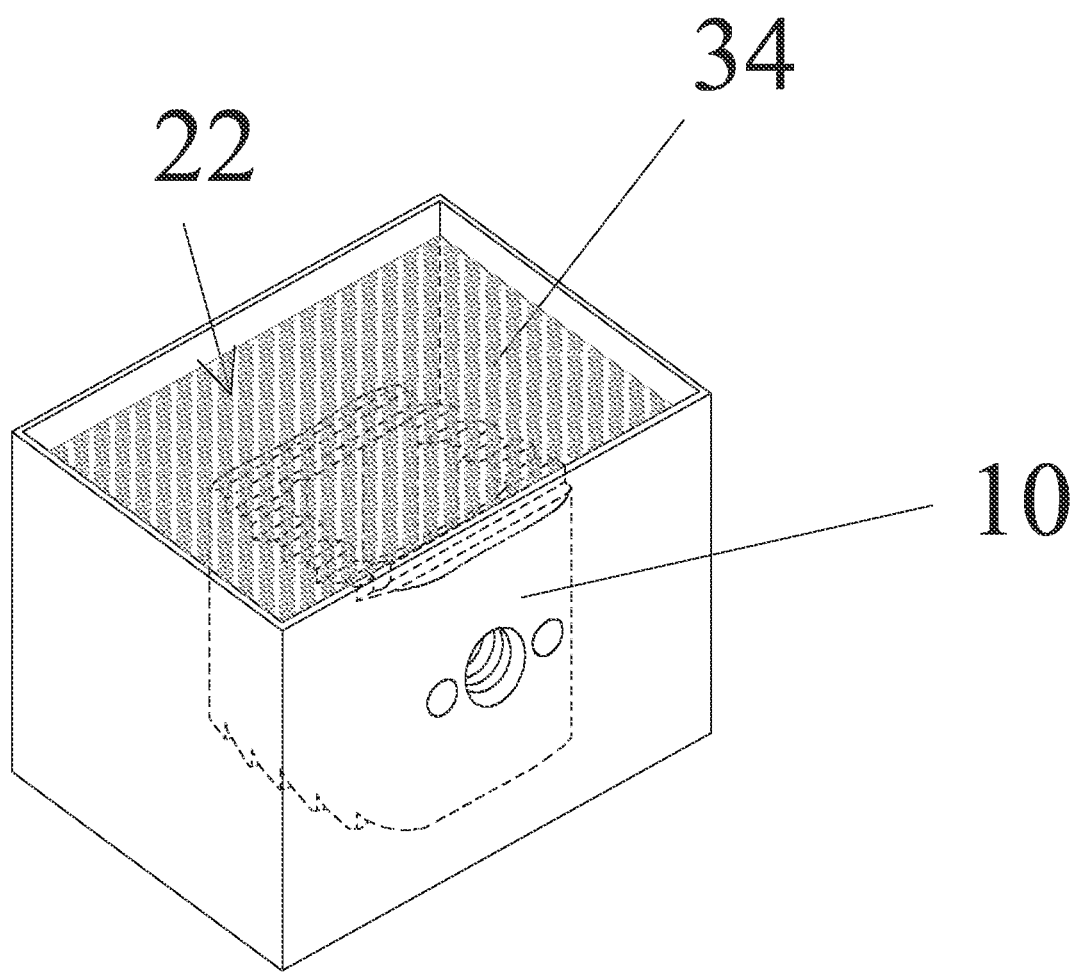
FIG. 7 is an exploded view of a pre-packaged spinal implant made according to the present invention in a liquid filled sterile container.

With reference to FIG. 7, a view of the prepackaged spinal implant made according to the present invention is shown wherein the device 10 is stored in a clear liquid filled sterile container 34. This liquid filled sterile container 34 has a spinal implant device 10 either wrapped 20 or coated 22 but placed in a fluid or liquid that ensures that the stem cell 21 viability is maintained during shipping. Again, in this method of pre-manufacture, the spinal implant 10 must be made in a sterile or clean environment or sterilized prior to being placed in the container and prior to being coated or wrapped with the stem cell material in such a fashion that the stem cells are not damaged and remain viable so that when the surgeon implants the spinal device, the stem cells are active and capable of generating tissue regeneration in a rapid and fast healing manner.

FIG. 8 is a perspective view of a spinal implant device 10 shown being spray coated with a mist 22 laden with stem cells 21 from a spray nozzle container 42 prior to being inserted into a patient. This mist 22 laden with stem cells 21 can be applied in the surgical room if so desired.

Figure 9:
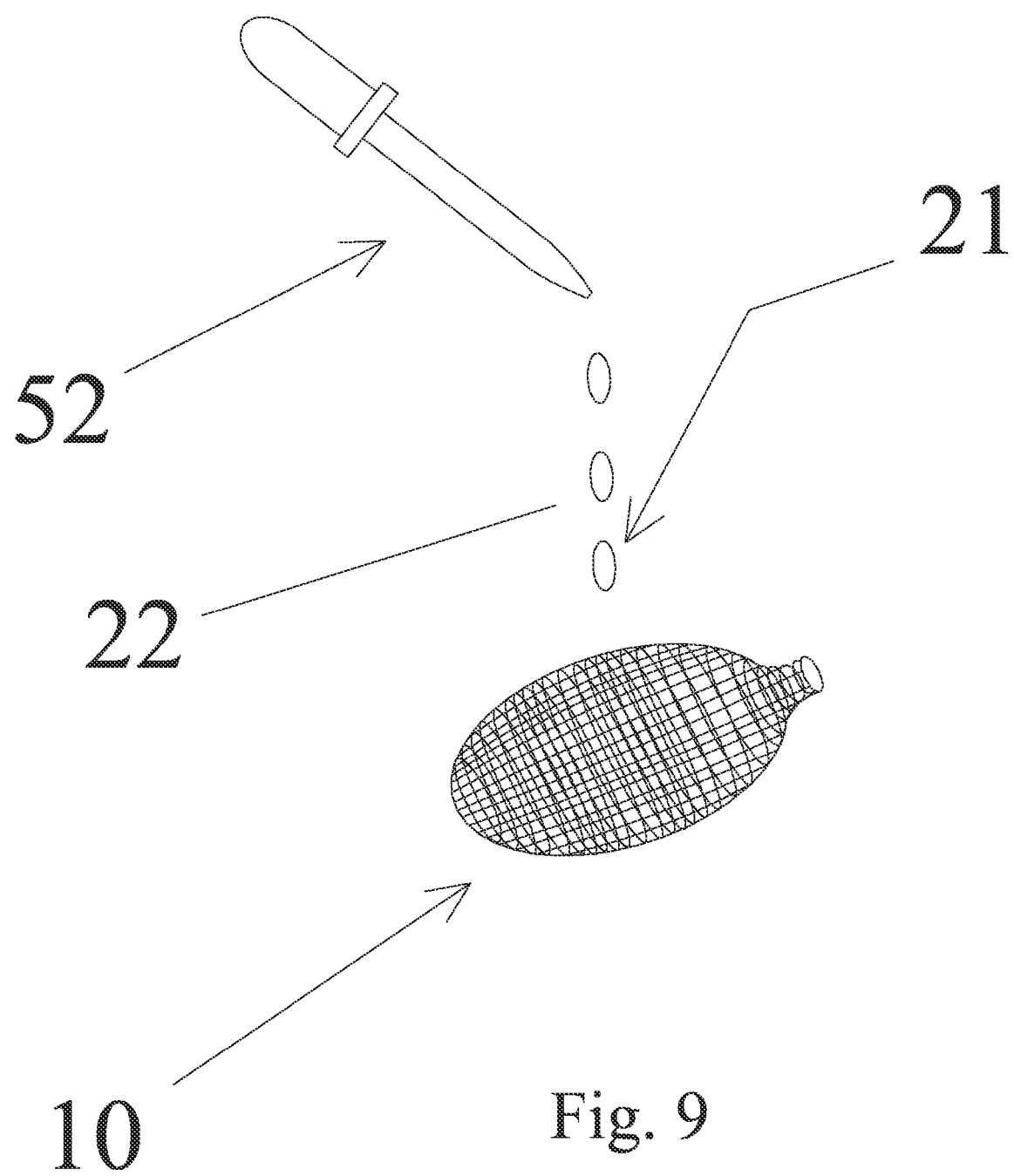
FIG. 9 is a perspective view of an alternative embodiment of the present invention using droplets to apply the stem cells.

In FIG. 9 the implant device of FIG. 1*k* is shown being coated with stem cell 21 laden drops 22 from a liquid dropper 52.

Figure 10:
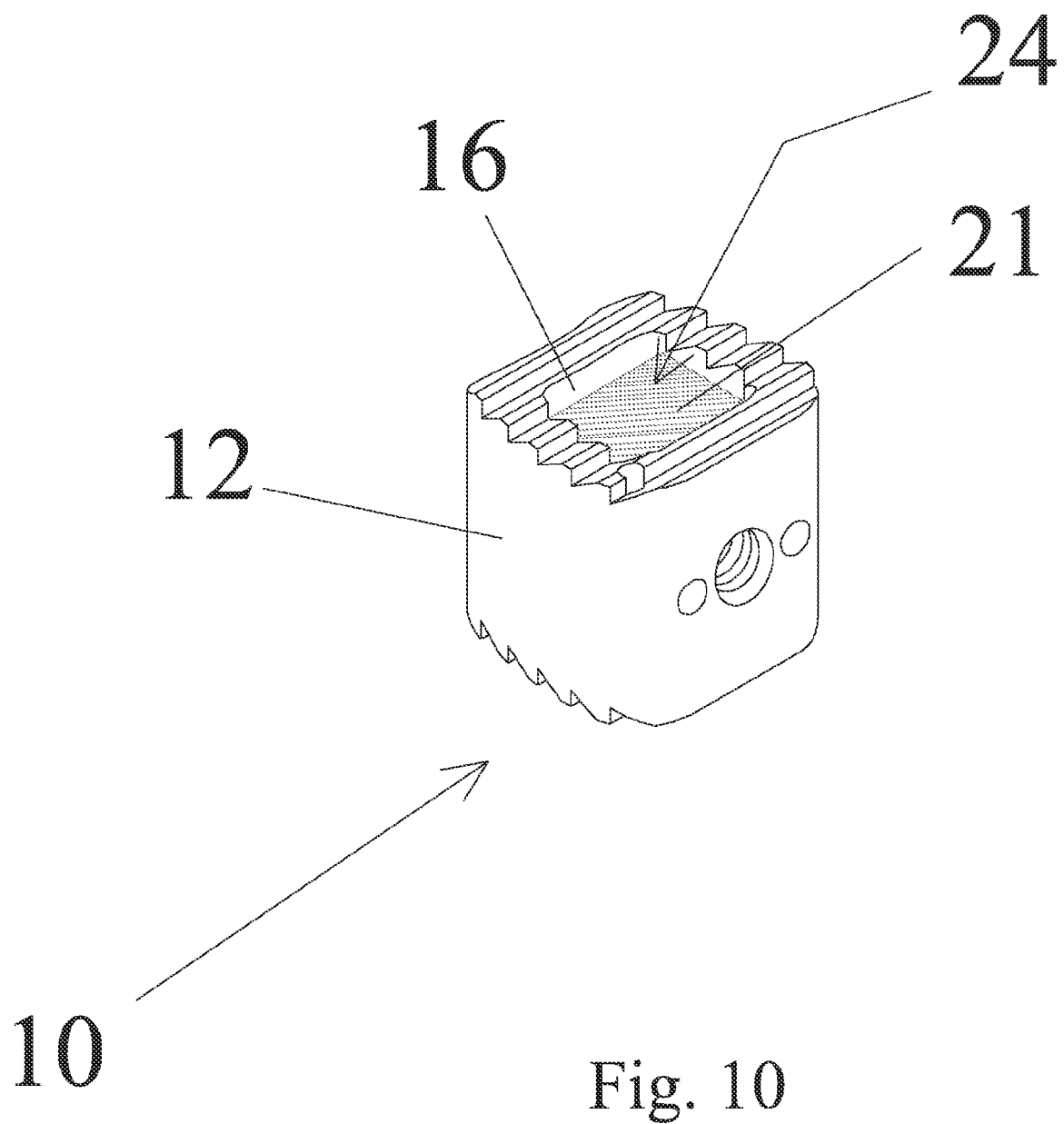
FIG. 10 is a perspective view of an alternative embodiment of the present invention showing the stem cells molded into a gelatinous plug.

In FIG. 10 the stem cells 21 are molded into a gelatinous plug 24 that fills a hollow portion or channel 16 of the device of the implant 10.

Referring back to FIGS. 1*a*-1*k*, the spinal implant 10 has a body structure 12 made out of either a metallic material or a synthetic material. If made out of synthetic plastic material, it is preferred that the synthetic implantable grade plastic be either a thermoset or a thermoplastic material. A number of suitable thermoplastic materials are available for implanting such as polyether ether kethone, polyethylene, ultra high molecular weight polyethylene, polysulfone and any number of other materials.

Alternatively, the implant body structure 12 can be made out of a metallic material that is suitable for implanting. As shown, titanium or stainless steel materials are very suited for spinal implant devices. As shown, the implantable device 10 formed as a spinal implant is designed to either be anchored to the spinal structure or implanted by providing holes 15 or openings 15 through which threaded fasteners can be screwed directly into the bone structure if so desired. Alternatively, the implantable device 10 can be unanchored and simply placed between vertebrae and held in place by and between adjacent vertebrae of the spinal skeletal structure. When held in this fashion, it is recommended that the upper surface 11 and lower exterior surface 13 have jagged or serrated teeth 17 configured to help hold the device 10 in place.

When the device 10 is made with a body structure 12 having a fixation surface like the saw teeth 17 it is no problem for this structure to be wrapped with a stem cell laden sheet or skin-like membrane 20 or alternatively to be coated with a coating 22 of stem cells 21 at the surgical site. When this is done, the stem cell 21 being a wrap 20 of rather thin skin-like membrane simply will conform to the underlying teeth 17 or ridges, as shown in FIG. 6, and therefore help assist and not impede the securing of the device 10 between the vertebrae.

The spinal implant device 10 as presented according to the present invention enables a variety of methods to be used for surgically treating a patient with a spinal defect which includes the steps of providing a spinal implant according to the present invention, preparing the patient to receive the spinal implant by surgically exposing the area to receive the spinal implant. The spinal implant preferably being a synthetic or metallic body structure or a combination of those materials is coated or wrapped around the body structure of the spinal implant with a coating or wrapping laden with viable stem cells. Once the coating or wrapping is achieved, if done at the surgical site, the device 10 is implanted with the coated or wrapped spinal implant 10 is positioned into the spinal skeletal structure of the patient, the surgical wound is then sutured and the patient is sent into a recovery room. One additional step is if the stem cell coating 22 or wrap 20 is in a dehydrated condition for shipping and storage, it may be necessary to hydrate the stem cells 21 with a liquid before wrapping or coating the implant 10. If this is accomplished, the stem cell wrap or membrane 20 becomes far more pliable and easier to conform to the outer surface of the body structure 12 of the spinal implant 10. If the spinal implant 10 is pretreated with a coating 22 or wrapping 20 laden with stem cells 21, then the procedure is similar however the surgeon does not need to wrap the implant body structure because it will have been previously done at the manufacture site in such a case, the stem cells 21 if already hydrated can be placed directly into the patient. Alternatively, if they require hydrating this additional step of providing a liquid to the coating or wrap laden body structure will need to be accomplished in order to rehydrate the stem cells 21 within the coating 22 or wrap 20.

As previously mentioned, the spinal implant 10 according to the present invention can be packaged in a variety of kits and provided to the surgeon either as separate components which are either wrapped or coated in the surgical suite or alternatively are pre-coated or wrapped at the manufacturing site, in either event, the present invention provides a unique and useful way of treating a spinal implant device with a material laden with viable stem cells in an attempt to accelerate bone regeneration and fusing of the implant 10 between vertebrae if so desired. While the present invention shows a variety of exemplary spinal implants 10, it is understood that any number of spinal implants 10 having a synthetic or metallic or combination of materials can be coated or wrapped and these variations are considered in the scope of the present invention. As previously mentioned, the spinal implant body structure 12 may include apertures 16 to provide additional biological material to facilitate in the fusing of the implant 10 to the skeletal bone structure, in such a case a paste of bone tissue may be provided within the aperture or channel 16 of the body structure 12 of the implant 10. Alternatively, cadaver bone could be used within the implant 10, as such these are considered also within the scope of the present invention and they facilitate the fusing of the spinal implant 10 in combination with the use of a coating 22 or wrap 20 laden with stem cells 21. It must be appreciated any of the implant devices shown in FIGS. 1a-1k can be wrapped or coated or plugged with a stem cell laden material and the use of the exemplary implant device of FIG. 1a was not intended to be limiting, but rather exemplary of the present invention. It is believed significant that the implants illustrated in FIGS. 1a-1j are made of a solid synthetic implantable plastic or metal or a combination of the two materials that is non-porous and inflexible. The implant of FIG. 1k is a woven porous implantable device and as such is in a separate and otherwise distinct class from the others and while all are believed novel when combined with stem cells the group from FIGS. 1a-1j are clearly unique spinal implant devices treated with a stem cell wrap, plug or coating that otherwise have no favorable porosity from which the stem cells can attach themselves.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A spinal implant device comprising:
a synthetic or metallic implant body structure for insertion on or into the skeletal spinal structure;
stem cells on a stem cell laden thin membrane, when hydrated, forming a skin-like wrap fixed or adhered onto exterior outer surfaces and conforming to the exterior outer surfaces on the synthetic or metallic implant body structure.

2. The spinal implant of claim 1 further comprises:
an aperture or channel incorporated in the implant body structure.

3. The spinal implant of claim 1 wherein the body structure is made of a synthetic implantable grade plastic.

4. The spinal implant of claim 3 wherein the synthetic plastic is an implantable grade thermoplastic material.

5. The spinal implant of claim 4 wherein the thermoplastic material is one of PEEK (polyether ether ketone), polyethylene, ultra high molecular weight polyethylene, acetal copolymer, polyphenylsulfone, polysulfone, polythermide, implantable grade lennite UHME-PE.

6. The spinal implant of claim 5 wherein the implantable grade thermoplastic is polyether ether ketone.

7. The spinal implant of claim 1 wherein the implant body structure is made of titanium.

8. The spinal implant of claim 1 wherein the implant body structure is made of stainless steel.

9. The spinal implant of claim 1 wherein the implantable device is unanchored to the spinal structure and held in place by and between adjacent vertebrae.

10. The spinal implant of claim 1 wherein the spinal implantable device is wrapped with a stem cell laden membrane at the surgical site.

11. The spinal implant of claim 1 wherein the spinal implantable device is wrapped with a stem cell laden membrane coated with the stem cells at a manufacturing site by having the implant body structure being sterilized, then wrapped in a sterile environment and sealed in a sterile packaging for later shipment and use.

12. The spinal implant of claim 1 wherein the stem cell wrap is re-hydrated at the time of use.

13. The spinal implant device of claim 1 wherein the skin-like wrap when fixed or adhered onto the exterior surface covers the entire exterior surface and is pliable to conform into any projections or ridges on the implant body structure.

14. A spinal implant device comprising:
- a synthetic non-metallic implant body structure for insertion on or into the skeletal spinal structure;
- stem cells on a stem cell laden sheet made of a thin membrane, when hydrated, forming a skin-like wrap fixed or adhered onto exterior outer surfaces and conforming to the exterior outer surfaces on the synthetic non-metallic implant body structure.

15. The spinal implant of claim 14 further comprises:
- an aperture or channel incorporated in the implant body structure.

16. The spinal implant of claim 14 wherein the body structure is made of a synthetic implantable grade plastic.

17. The spinal implant of claim 16 wherein the synthetic plastic is an implantable grade thermoplastic material.

18. The spinal implant of claim 17 herein the thermoplastic material is one of PEEK (polyether ether ketone), polyethylene, ultra high molecular weight polyethylene, acetal copolymer, polyphenylsulfone, polysulfone, polythermide, implantable grade lennite UHME-PE.

19. The spinal implant of claim 18 wherein the implantable grade thermoplastic is polyether ether ketone.

20. The spinal implant device of claim 14 wherein the skin-like wrap when fixed or adhered onto the exterior surface covers the entire exterior surface and is pliable to conform into any projections or ridges on the implant body structure.

* * * * *